United States Patent
Wang

(10) Patent No.: US 11,033,213 B2
(45) Date of Patent: Jun. 15, 2021

(54) SECURE INJECTION NEEDLE

(71) Applicant: BERPU MEDICAL TECHNOLOGY CO., LTD, Wenzhou (CN)

(72) Inventor: Xingguo Wang, Wenzhou (CN)

(73) Assignee: BERPU MEDICAL TECHNOLOGY CO., LTD, Wenzhou (CN)

( * ) Notice: Subject to any disclaimer, the term of this patent is extended or adjusted under 35 U.S.C. 154(b) by 133 days.

(21) Appl. No.: 16/349,285

(22) PCT Filed: Dec. 15, 2016

(86) PCT No.: PCT/CN2016/110122
§ 371 (c)(1),
(2) Date: May 13, 2019

(87) PCT Pub. No.: WO2018/086192
PCT Pub. Date: May 17, 2018

(65) Prior Publication Data
US 2019/0343439 A1 Nov. 14, 2019

(30) Foreign Application Priority Data
Nov. 11, 2016 (CN) .......................... 201610993369.6

(51) Int. Cl.
*A61B 5/15* (2006.01)
*A61B 5/153* (2006.01)
*A61M 5/32* (2006.01)

(52) U.S. Cl.
CPC .... *A61B 5/150541* (2013.01); *A61B 5/15003* (2013.01); *A61B 5/153* (2013.01); *A61B 5/150572* (2013.01); *A61M 5/3216* (2013.01)

(58) Field of Classification Search
CPC .......... A61B 5/150541; A61B 5/15003; A61B 5/150572; A61B 5/153; A61M 5/3216; A61M 5/32
See application file for complete search history.

(56) References Cited

U.S. PATENT DOCUMENTS 5,242,417 A 9/1993 Paudler
6,582,397 B2 * 6/2003 Alesi ................... A61M 5/3216
604/110
(Continued)

FOREIGN PATENT DOCUMENTS

CN 101282755 A 10/2008
CN 202724375 U 2/2013
(Continued)

*Primary Examiner* — Bhisma Mehta
*Assistant Examiner* — Rachel T. Smith
(74) *Attorney, Agent, or Firm* — Bayramoglu Law Offices LLC

(57) ABSTRACT

An injection needle includes a needle hub and a needle tube. The needle hub is connected to a safety protective cover by an elastic flip mechanism. Two symmetrically-distributed needle hub hooks are provided on a side wall of the needle hub. Two symmetrically-distributed protective cover snaps are provided in a hollow inner cavity of the safety protective cover. The two protective cover snaps cooperates with the two needle hub hooks. Protective cover snap stoppers are provided on outer sides of the two protective cover snaps. The injection needle employs the two needle hub hooks disposed on the side wall of the needle hub and cooperate with the two protective cover snaps disposed in the inner cavity of the safety protective cover.

10 Claims, 20 Drawing Sheets

(56) References Cited

U.S. PATENT DOCUMENTS

| | | | |
|---|---|---|---|
| 8,172,809 B2 * | 5/2012 | Ferguson | A61B 5/150496 |
| | | | 604/192 |
| 9,457,155 B2 * | 10/2016 | Mathiasson | A61M 5/3204 |
| 2017/0182259 A1 * | 6/2017 | Fukushi | B65D 25/108 |

FOREIGN PATENT DOCUMENTS

| | | | | |
|---|---|---|---|---|
| CN | 202724380 U | 2/2013 | | |
| CN | 203196091 U | 9/2013 | | |
| CN | 103908267 A | 7/2014 | | |
| CN | 103908710 A | 7/2014 | | |
| CN | 203694278 U | 7/2014 | | |
| WO | WO-2016087868 A1 * | 6/2016 | | A61M 5/2466 |

\* cited by examiner

SECURE INJECTION NEEDLE

CROSS REFERENCE TO THE RELATED APPLICATIONS

This application is the national phase entry of International Application No. PCT/CN2016/110122, filed on Dec. 15, 2016, which is based upon and claims priority to Chinese Patent Application No. 201610993369.6, filed on Nov. 11, 2016, the entire contents of which are incorporated herein by reference.

TECHNICAL FIELD

The present invention relates to the technical field of medical instruments, and specifically to safety injection needles.

BACKGROUND

Document 1 is a patent application No. 201410114478.7 filed by Applicant Wenzhou Beipu Science & Technology Co. Ltd. on the filing date Mar. 26, 2014. The patent application discloses "Safety Blood Collecting Needle", comprising a needle hub and a double-headed needle tube running through the needle seat, the double-headed needle tube having a venous puncture needle at one end and a cannula needle at the other end, wherein the safe blood collecting needle further comprises a safety sheath, a connecting mechanism and a snap seat, the snap seat is fixed on the needle hub, the safety sheath is connected to the snap seat by the connecting mechanism, the safety sheath may turn with the connecting mechanism as a center, the safety sheath is a hollow cavity, and at least one needle tube safety hook is provided in the cavity. The safety sheath is a cylindrical member, a side of a side wall of the safety sheath facing the needle is provided with an opening, the length of the opening is greater than the length of the needle, a protective flap is formed respectively at positions of the sidewall of the safety sheath located on both sides of the opening, and the two protective flaps are oppositely disposed. Two needle tube safety hooks are disposed in the safety sheath, roots of hook bodies of the needle tube safety hooks are located on an inner sidewall of the safety sheath between the two protective flaps, an acute angle which exactly faces the inner sidewall of the safety sheath between two protective flaps is formed at a bending point of the hook body of the needle tube safety hook, the hook bodies of the two needle tube safety hooks are opposite in direction, and the needle tube safety hooks may hook on the needle tube. Two sheath snaps are disposed in the safety sheath, the sheath snaps each a protruding block, the two sheath snaps are oppositely positioned, the sheath snaps are disposed on the inner sidewalls of the protective flaps, the snap seat is provided with two snap mouths corresponding to the sheath snaps in shape, and the sheath snaps may be snapped on the snap mouths. The snap seat is a ring-like member disposed around the outer surface of the needle hub, and the ring corresponds to the outside of the needle hub in size and shape. The snap seat is a hollow cavity and disposed around the outer surface of the needle hub, and the cavity corresponds to the needle hub in size and shape. The sheath snaps are disposed on the inner sidewall of the safety sheath adjacent to the connecting mechanism. The connecting mechanism comprises a flip mechanism and an elastic mechanism, both ends of the elastic mechanism are respectively connected to both ends of the flip mechanism, and the elastic mechanism is located exactly below the flip mechanism. The venous puncture needle is externally provided with a puncture needle cap which is snapped on the needle hub; the cannula needle is externally provided with a cannula needle cap which is snapped on the needle hub.

Document 2 is a patent application No. 201410114477.2 filed by Applicant Wenzhou Beipu Science & Technology Co. Ltd. on the filing date Mar. 26, 2014. The patent application discloses "Safety Injector", comprising a barrel and a needle, the needle includes a needle hub and a needle tube, wherein the safety injector further comprises a safety sheath, a connecting mechanism and a snap seat, the snap seat is fixed on the needle hub, the safety sheath is connected to the snap seat by the connecting mechanism, the safety sheath may turn with the connecting mechanism as a center, the safety sheath is a hollow cavity, and at least one needle tube safety hook is provided in the cavity. The safety sheath is a cylindrical member, a side of a side wall of the safety sheath facing the needle is provided with an opening, the length of the opening is greater than the length of the needle, a protective flap is formed respectively at positions of the sidewall of the safety sheath located on both sides of the opening, and the two protective flaps are oppositely disposed. Two needle tube safety hooks are disposed in the safety sheath, roots of hook bodies of the needle tube safety hooks are located on an inner sidewall of the safety sheath between the two protective flaps, an acute angle which exactly faces the inner sidewall of the safety sheath between two protective flaps is formed at a bending point of the hook body of the needle tube safety hook, the hook bodies of the two needle tube safety hooks are opposite in direction, and the needle tube safety hooks may hook on the needle tube. Two sheath snaps are disposed in the safety sheath, the sheath snaps each a protruding block, the two sheath snaps are oppositely positioned, the sheath snaps are disposed on the inner sidewalls of the protective flaps, the snap seat is provided with two snap mouths corresponding to the sheath snaps in shape, and the sheath snaps may be snapped on the snap mouths. The snap seat is a ring-like member disposed around the outer surface of the needle hub, and the ring corresponds to a lower portion of the needle hub in size and shape. The snap seat is a hollow cavity and disposed around the outer surface of the needle hub, and the cavity corresponds to the needle hub in size and shape. The sheath snaps are disposed on the inner sidewall of the safety sheath adjacent to the connecting mechanism. The connecting mechanism comprises a flip mechanism and an elastic mechanism, both ends of the elastic mechanism are respectively connected to both ends of the flip mechanism, and the elastic mechanism is located exactly below the flip mechanism. The needle is externally provided with a needle cap whose bottom is sleeved around the snap seat.

It can be seen from the above prior art documents that the current safety injection needles employ a lateral safety sheath structure, a hook body cooperating with the needle tube of the injection needle is disposed in the safety sheath, the hook body engages with the needle tube to achieve relative securement of safety sheath and the needle tube, the needle tube is hidden in the safety sheath, and finally protection of the injection needle is achieved, and injury caused by piercing can be effectively avoided.

During clinical use, the safety injection needles disclosed in the prior art still have the following problems during use: 1. a larger force must be applied when the safety sheath is fitted, and medical care providers operate difficultly when a large batch of safety sheaths are clinically used; 2. The snap-fitting between the hood body structure and the needle tube has a certain defect so that when a certain external force is received, the two are likely to disengage, and the stability and safety are both undesirable; 3. When the safety sheath is snap-fitted with the needle tube, the needle tube still remains in a straight state, the engagement strength between the hook body and the needle tube is not large, the needle tube still has room to move in the hook body so that the locking structure of the needle tube exhibits a poor stability; 4. To conveniently lock the needle tip within the safety sheath after use, either a locking member is disclosed, as is the case in many patents, or the needle hub of ordinary injection needle is enlarged. The added material costs for such a disposable product becomes very large, because waste of plastic materials and the production costs are increased.

SUMMARY

An object of the present invention is to provide a safety injection needle, wherein hook members are disposed on a sidewall of the needle hub to cooperate with snap members disposed in a safety protective cover adjacent and opposite to the hook members and have an elastic root portion. The designed structure enables the elastic root portion to elastically and easily open to allow the safety protective cover to fit in, a thrust needed is about 0.5N, and very comfortable single-hand operation is enabled upon clinical use. If the safety protective cover is to be opened after it is fitted, the elastic root portion of the snaps tilts in a direction in which the needle hub hook member applies a force to generate a very strong anti-pull force so that the safety protective cover is very hard to open, thereby overcoming drawbacks and shortcomings existing in the prior art. The design of the ordinary needle hub is used to minimize members for achieving the safety function, reduce the volume of the product, and make the product lower in costs and more environmentally-friendly.

To achieve the above object, the present invention employs the following technical solution: a safety injection needle, comprising an injection needle consisting of a needle hub and a needle tube, the needle hub is connected to a safety protective cover via an elastic flip mechanism, two symmetrically-distributed needle hub hooks are disposed on a sidewall of the needle hub, the safety protective cover is an elongated structure on the whole, an inner cavity of the safety protective cover is hollow, a lower end of the safety protective cover is connected to one end of the elastic flip mechanism, the other end of the elastic flip mechanism is fixedly connected to the sidewall of the needle hub, an upper end of the safety protective cover is in a suspended shape, the safety protective cover flips as the elastic flip mechanism flips, a side of the safety protective cover adjacent to the needle tube forms an opening, the other side of the safety protective cover opposite to the opening forms a closed surface, two symmetrically-distributed protective cover snaps with elastic root portions are disposed in the hollow inner cavity of the safety protective cover, the two protective cover snaps cooperate with the two needle hub hooks, and a protective cover snap stopper is disposed on the outside of each of the protective cover snaps.

The present invention discloses a safety injection needle employing a dual needle hub hook structure disposed on a sidewall of the needle hub and cooperating with dual protective cover snaps disposed in the inner cavity of the safety protective cover. The snap-fitting process of the protective cover snaps and needle hub hooks is easy and convenient, the needed thrust only needs to be about 0.5N, and single-hand operation can be achieved. Protective cover snap stoppers are disposed on the outside of the protective cover snaps, and can effectively prevent the disengagement of the protective cover snaps from the needle hub hooks. The needle hub in the technology of the present invention still employs the design structure of a conventional needle hub with only the needle hub hooks being additionally provided. This structure may be formed in one time, and does not require the increase of the volume of the needle hub or increase of other components for snap-fitting the safety protective cover to achieve the function of the safety snaps. The structure effectively controls the costs, saves the material and simply and effectively achieves safe operations of the product. In addition, another advantage of conforming to the conventional needle hub lies in that the position of the needle hub is smaller. Upon product assembling, more products may be assembled on an assembly line one time with a higher production efficiency. The whole design of the product uses a concise structure to well achieve functional requirements, and stability and safety may both achieve an ideal effect.

DETAILED DESCRIPTION OF THE EMBODIMENTS

The present invention will be further described with reference to figures

Figure 1:
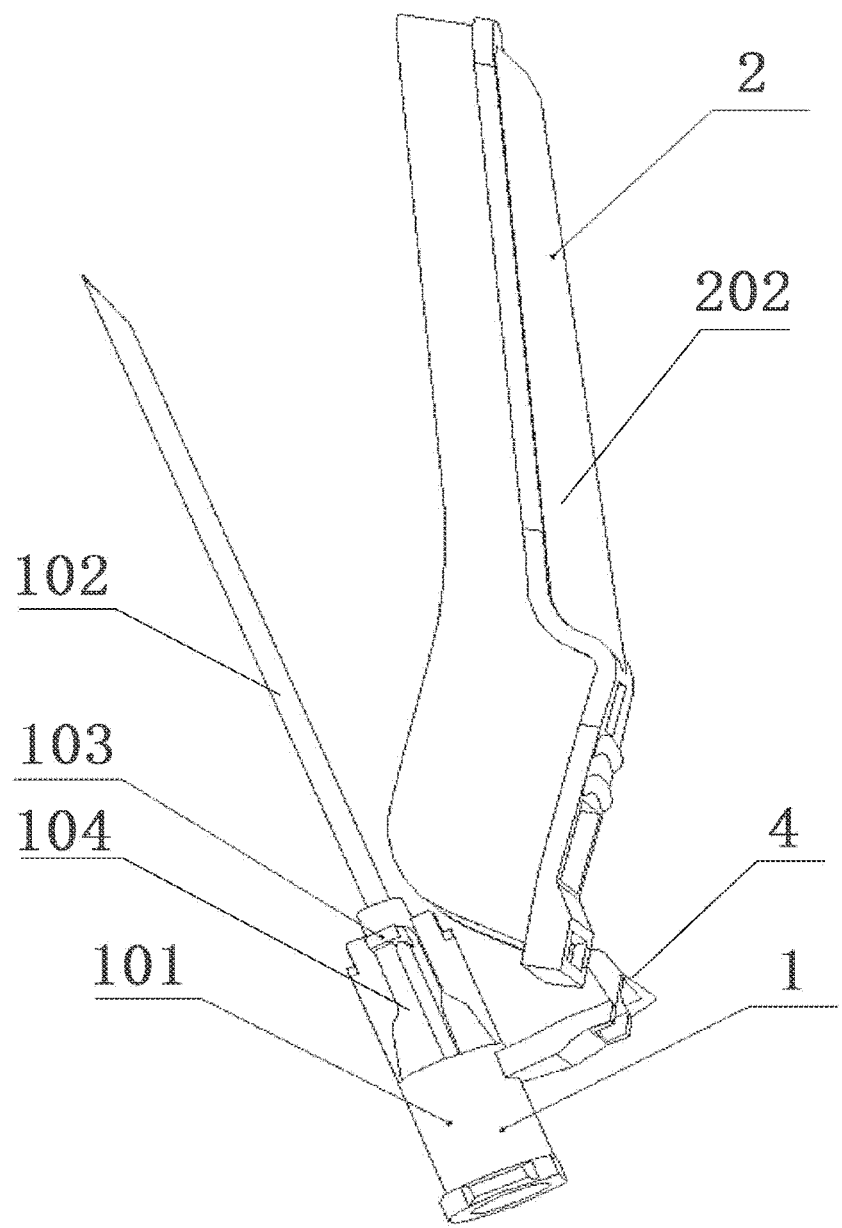
FIG. 1 is a schematic view showing the structure of a safety injection needle according to the present invention.
Figure 2:
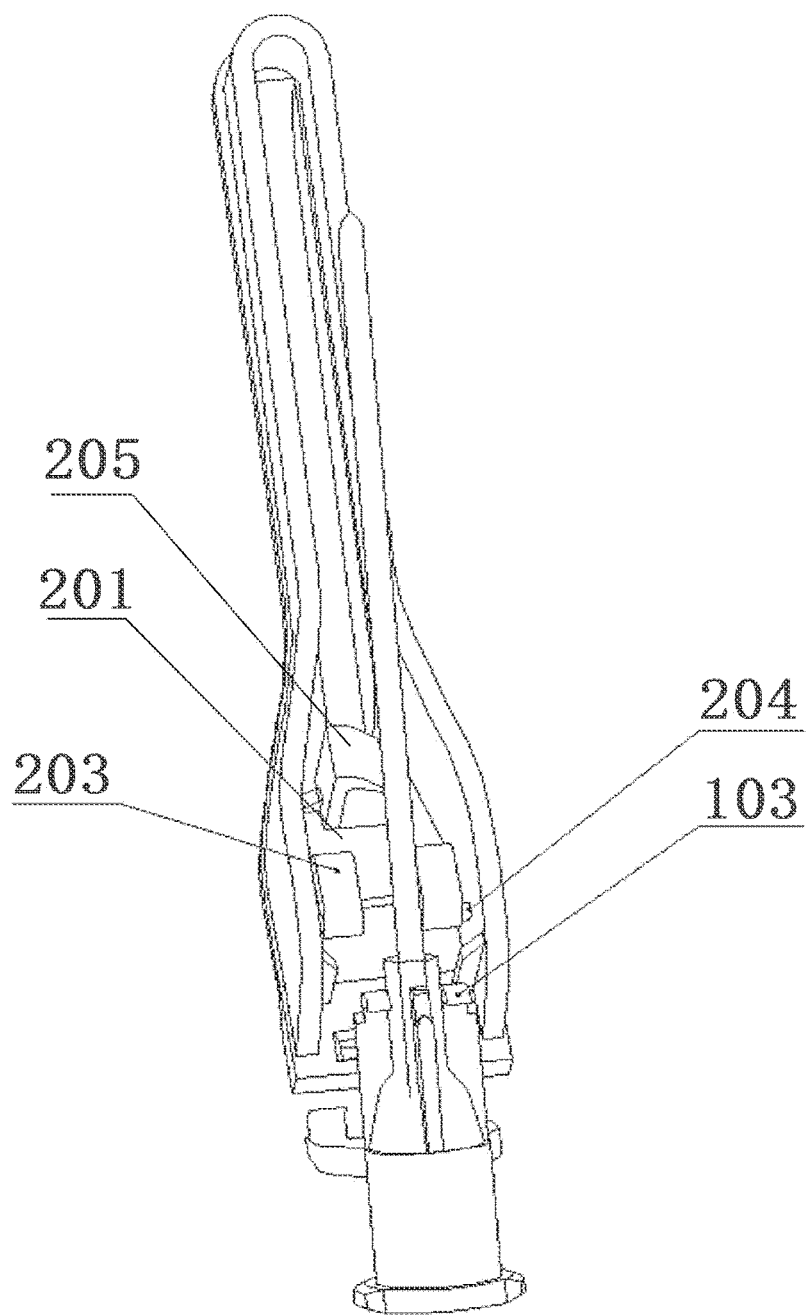
FIG. 2 is a perspective view of a safety injection needle according to the present invention.

The present invention discloses a safety injection needle. As shown in FIG. 1 and FIG. 2, it comprises an injection needle 1 consisting of a needle hub 101 and a needle tube 102. The safety injection needle differs from the prior art in that the needle hub 101 is connected to a safety protective cover 2 via an elastic flip mechanism 4, two symmetrically-distributed needle hub hooks 103 are disposed on a sidewall of the needle hub 101, the safety protective cover 2 is an elongated structure on the whole, an inner cavity of the safety protective cover 2 is hollow, a lower end of the safety protective cover 2 is connected to one end of the elastic flip mechanism 4, the other end of the elastic flip mechanism 4 is fixedly connected to the sidewall of the needle hub 101, an upper end of the safety protective cover 2 is in a suspended shape, the safety protective cover 2 flips as the elastic flip mechanism 4 flips, a side of the safety protective cover 2 adjacent to the needle tube 102 forms an opening 201, the other side of the safety protective cover 2 opposite to the opening 201 forms a closed surface 202, two symmetrically-distributed protective cover snaps 203 are disposed in the hollow inner cavity of the safety protective cover 2, the snaps 203 have an elastic root portion 2031 (without need for other materials, when the position and thinness of the snaps are made, injection molding can be performed to simultaneously make the snaps and the safety protective cover), the two protective cover snaps 203 cooperate with the two needle hub hooks 103, and a protective cover snap stopper 204 is disposed on the outside of each of the protective cover snaps 203.

Figure 19:
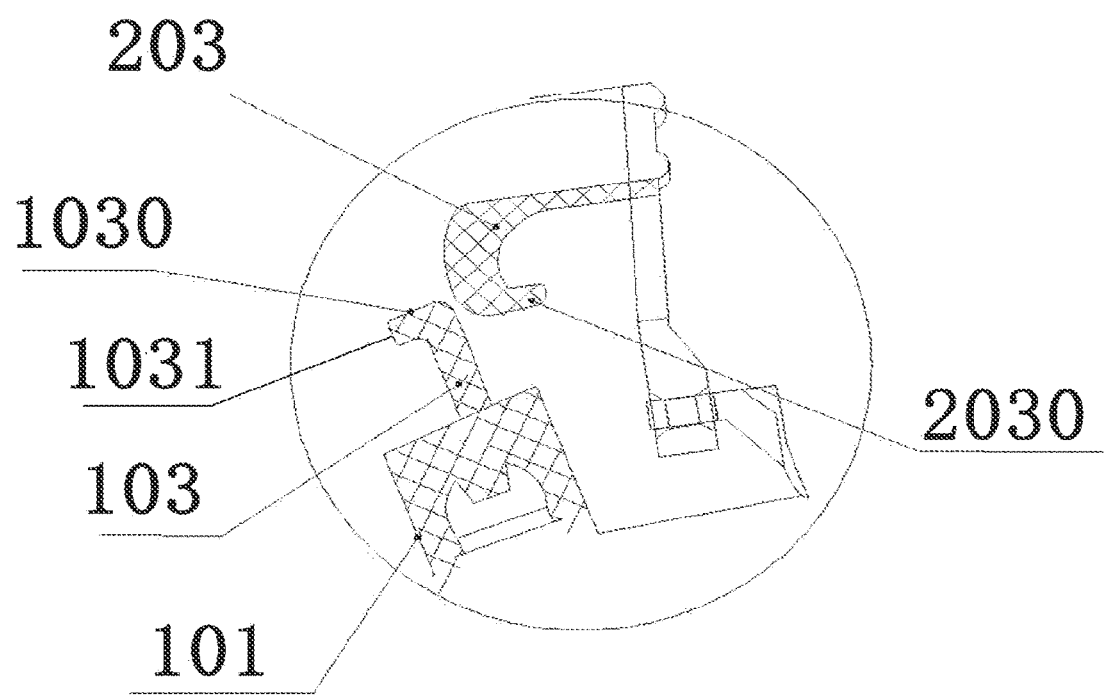
FIG. 19 is a schematic view of a first state of an engagement process of the snap hooks and protective cover snaps according to the present invention.
Figure 20:
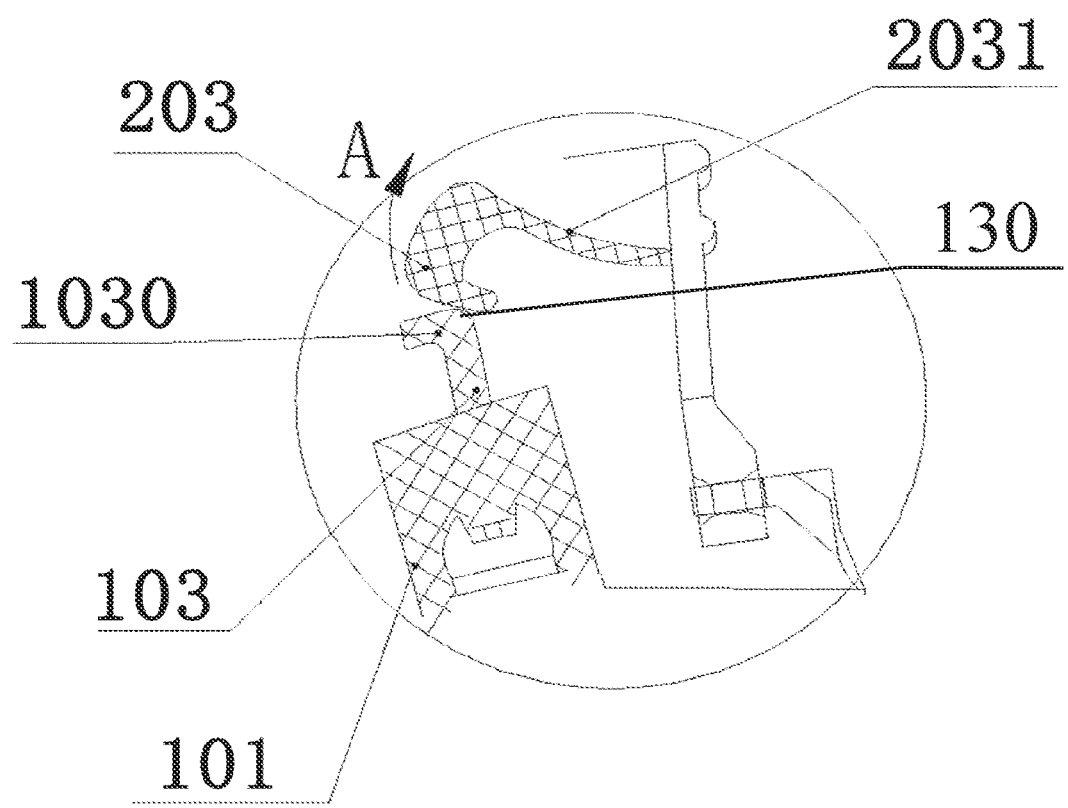
FIG. 20 is a schematic view of a second state of an engagement process of the snap hooks and protective cover snaps according to the present invention.
Figure 21:
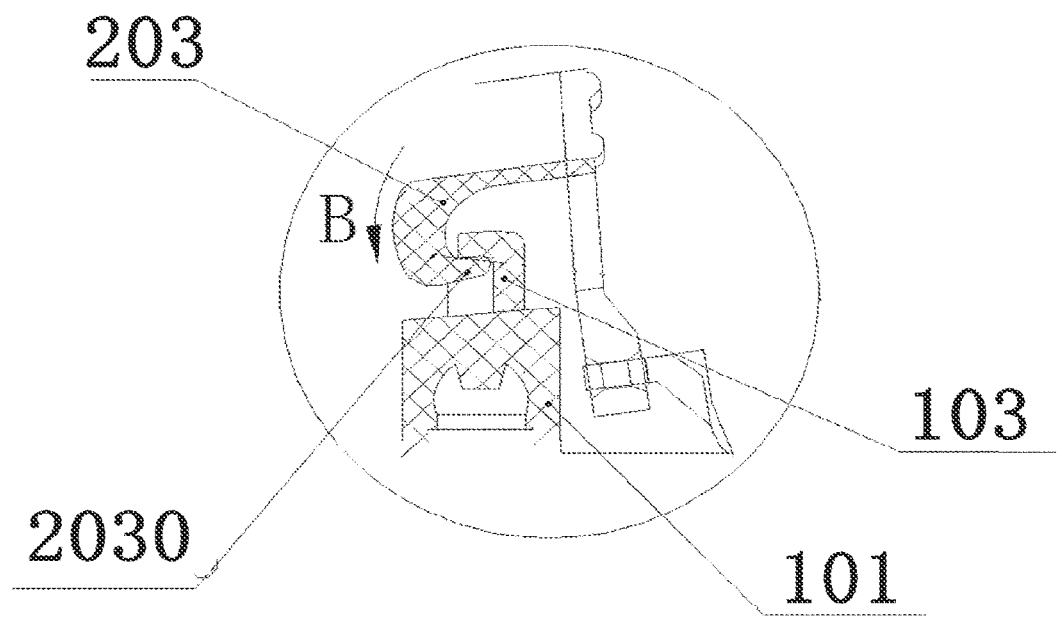
FIG. 21 is a schematic view of a third state of an engagement process of the snap hooks and protective cover snaps according to the present invention.

Upon implementation, an upper end portion of the needle hub hook 103 forms a hook end 1031 bent towards a side, the protective cover snaps 203 consist of an elastic root portion 2031 and a snap end 2030, the snap end 2030 of the protective cover snap 203 forms a bend towards the closed surface 202, initial contact points of the needle hub hook 103 and protective cover snap 203 are a bend of the hook end and a bend of the snap end 2030, and the hook end and the snap end 2030 bend in opposite directions. The structural design can ensure that upon initial contact of the needle hub hook 103 and protective cover snap 203, touch surfaces of the two are two arcuate bent surfaces or one of the touch surfaces is an arcuate bent surface, to reduce a thrust triggering engagement of the two to a minimum. Meanwhile, the protective cover snap 203 has an elastic root portion 2031; when the safety protective cover is fitted, the needle hub hook 103 abuts against the protective cover snap 203, the elastic root portion 2031 tilts in a direction that the needle hub hook 103 lifts (direction A of FIG. 20); when a hook top 130 lifts beyond the top of the snap 203, the protective cover snap 203 rebounds in the direction shown in FIG. 21, and is caught in the needle hub hook 103. Experiments prove that the catching force only needs to be about 0.5N. The technical feature cannot be achieved by products of the same type commercially available in the market. (See FIG. 19-FIG. 21 for partially enlarged views).

Figure 22:
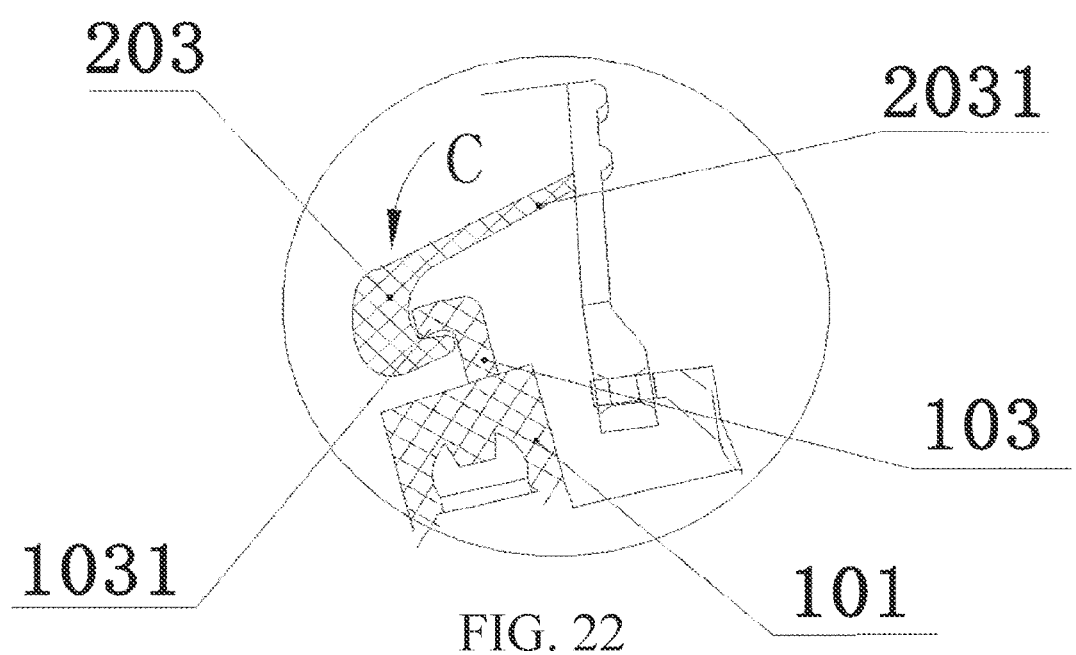
FIG. 22 is a schematic view of a fourth state of an engagement process of the snap hooks and protective cover snaps according to the present invention.

When an external force is applied to open the safety protective cover and the needle hub, the hook 103 pulls the snap 203 in the direction shown in FIG. 22, and the elastic root portion of the snap 203 tends to tilt in the direction C. At this time, the force for opening the safety protective cover and needle hub becomes: 1. a deforming and disengaging force of the head of the snap 203. It is possible to thicken the plastic of the head of the hook 203 so that it is very difficult to deform; 2. a force for pulling and breaking the elastic root portion 2031. It is very difficult to pull and break the plastic material; 3. the head of the hook 1030 deforms and disengages. But one side of the hook 103 is fixed on the needle hub and does not deform. To sum up, the opening force is very large.

Upon implementation, when the hook end 1031 engages with the snap end 2030, the protective cover snap stopper 204 limits the end of the protective cover snap 203 between the edge of the safety protective cover 2 and the needle hub so that the end of the protective cover snap 203 cannot deviate to left and right, preventing the protective cover snap 203 from sliding away from both sides of the needle hub hook 103. Furthermore, the protective cover snap 203 cooperates with the protective cover snap stopper 204 on both sides to form a continuous blocking structure for the needle hub hook 103. It can be seen from the above structure that after the hook end engages with the snap end through a reverse structure, it is possible to separate the two through an external force because the protective cover snap 203 may slide away from both sides of the needle hub hook 103. However, when both sides of the protective cover snap 203 are blocked by the protective cover snap stopper 204. This possibility is close to zero.

Upon specific implementation, the elastic flip mechanism 4 consists of a fixed connection plate 401 and a right-angle connection plate 402, the fixed connection plate 401 is fixedly connected to the sidewall of the needle hub 101, the other end of the fixed connection plate 401 is connected to one end of the right-angle connection plate 402, the other end of the right-angle connection plate is fixedly connected to a lower end of the safety protective cover 2, a fold line 403 is formed at a position where the fixed connection plate 401 is connected to the right-angle connection plate 402, and the right-angle connection plate 402 flips along the fold line 403.

Upon specific implementation, a reinforcing rib 104 is respectively disposed on the outer wall on both sides of an upper segment of the needle hub 101, and the needle hub hook 103 is disposed at a top end of the reinforcing rib 104.

Upon specific implementation, the closed surface 202 consists of an upper portion 2021 and a lower portion 2022, a continuous arc-shaped surface 2023 is disposed at a position where the upper portion 2021 is connected to the lower portion 2022, and an inner angle smaller than 178 degrees and larger than 120 degrees is formed between the lower portion 2021 and lower portion 202. The designed structure can ensure that the needle tube curves under a pressure in an engaged state, and forms a counteraction force to an inner wall of the enclosed surface 202, and increases the coefficient of firmness. Meanwhile, the designed structure can minimize the volume of the product and facilitate packing and transportation.

Upon specific implementation, a needle tube fixing hook 205 is disposed in the hollow inner cavity of the safety protective cover 2, and the needle tube fixing hook 205 cooperates with the needle tube 102.

Figure 3:
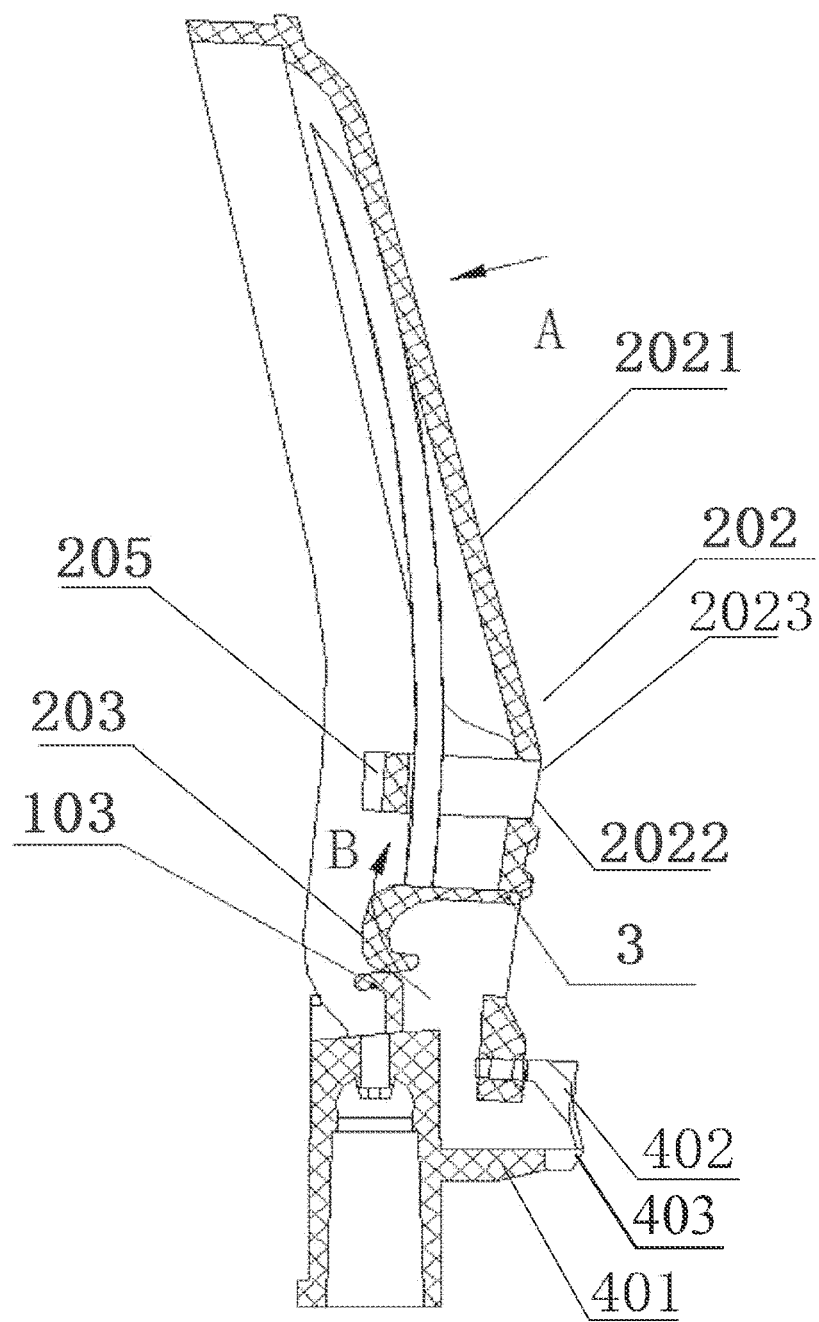
FIG. 3 is a diagram showing a first use state of the safety injection needle according to the present invention.
Figure 4:
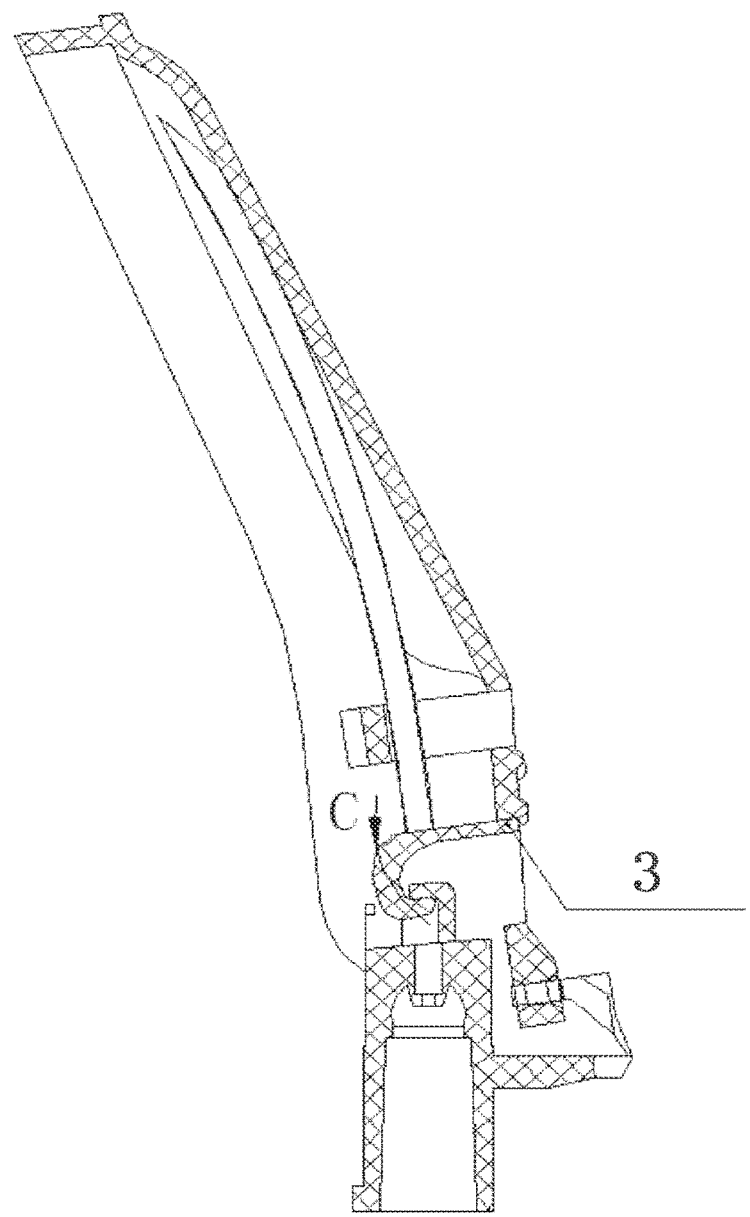
FIG. 4 is a diagram showing a second use state of the safety injection needle according to the present invention.

In specific implementation, as shown in FIG. 3, upon completion of injection, when the safety protective cover is pressed downward in a direction of a force-exerting point A, the protective cover snap is driven to displace in an arcuate trajectory. When the protective cover snap touches the needle hub hook, the protective cover snap will be blocked, deforms backward via a fulcrum 3 and forms an accumulated force B. As shown in FIG. 4, pressing continues; when an apex of the protective cover snap goes beyond an apex of the needle hub hook, the protective cover snap forms a direction force C under the release of the accumulated force B, holds and engaged with the needle hub hook under its action, and thereby the engagement action of the two. As shown in FIG. 4, the above whole process is action steps of engagement of the safety protective cover and the injection needle. Since the protective cover snap deforms under a force and completes engagement, the magnitude of the received force and deforming force affects the hand feeling of the operation. Since the deformation site of the protective cover snap is very thin, it is known from tests and calculation that the value of the force is very small, about 0.5N. The hand feeling of the operation is very slight, and great comfort is presented in clinical use.

Figure 5:
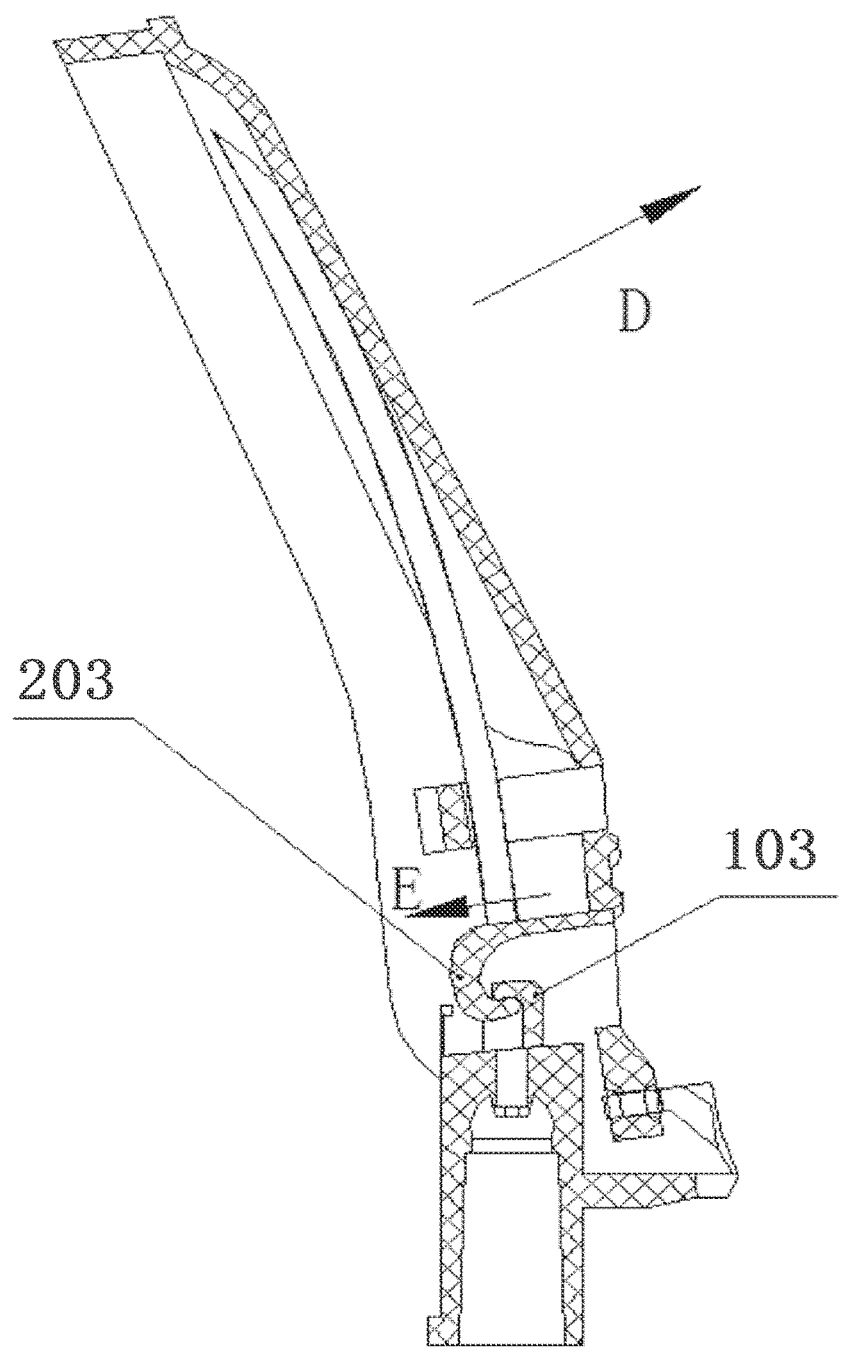
FIG. 5 is a diagram showing a third use state of the safety injection needle according to the present invention.
Figure 6:
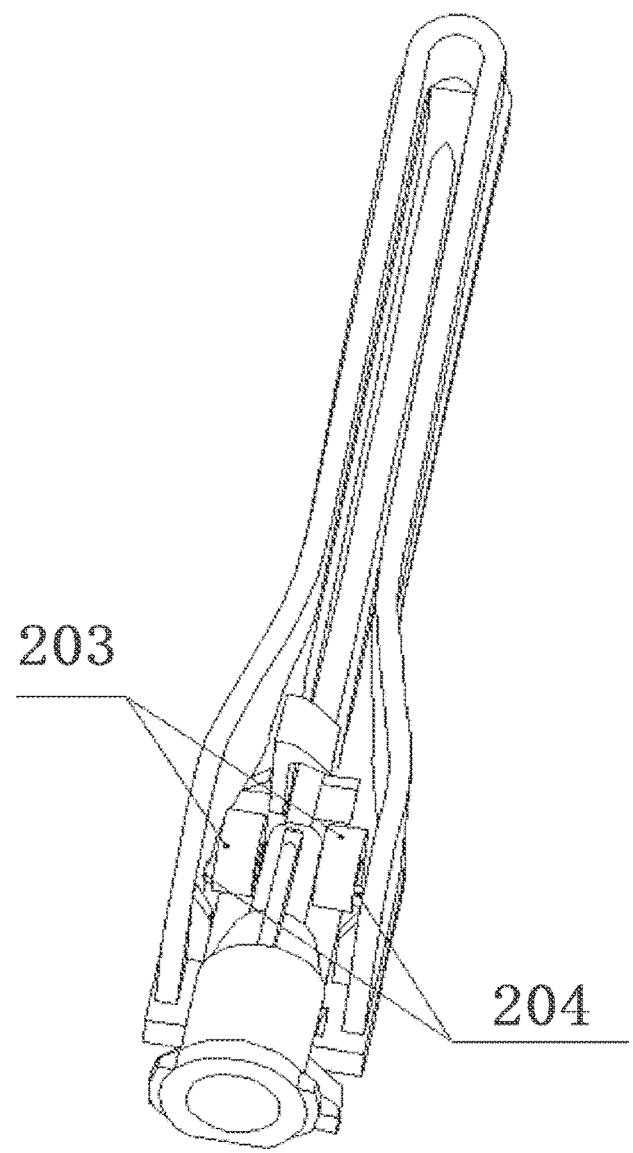
FIG. 6 is a schematic view showing a locked state of the injection needle and a safety protective cover according to the present invention.
Figure 7:
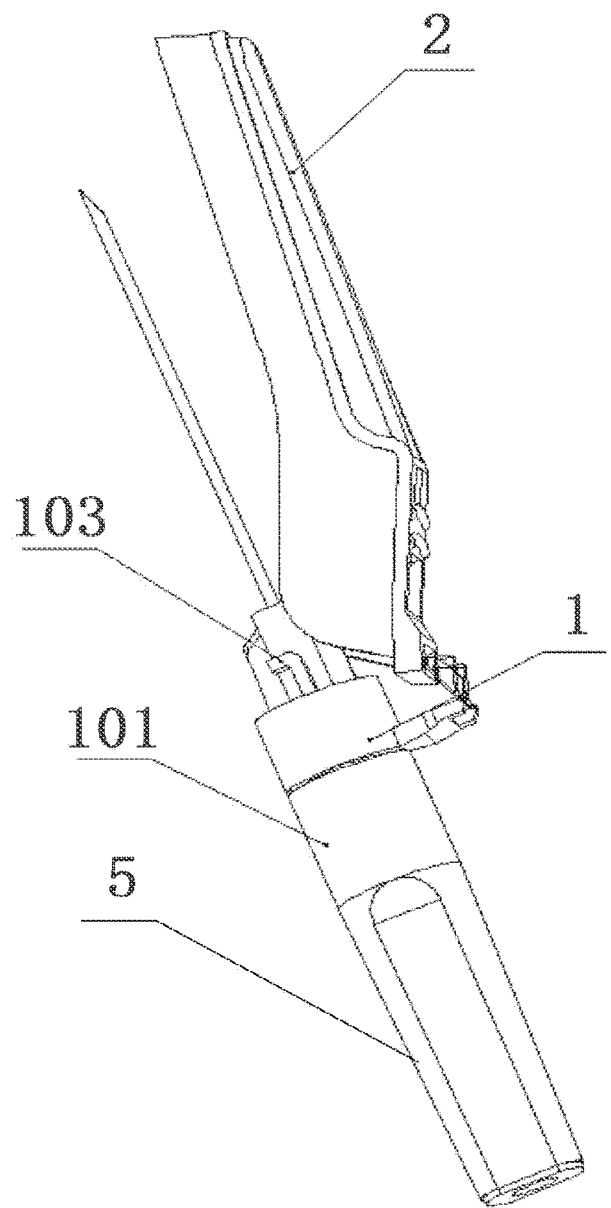
FIG. 7 is a schematic structural view of a first embodiment according to the present invention.
Figure 8:
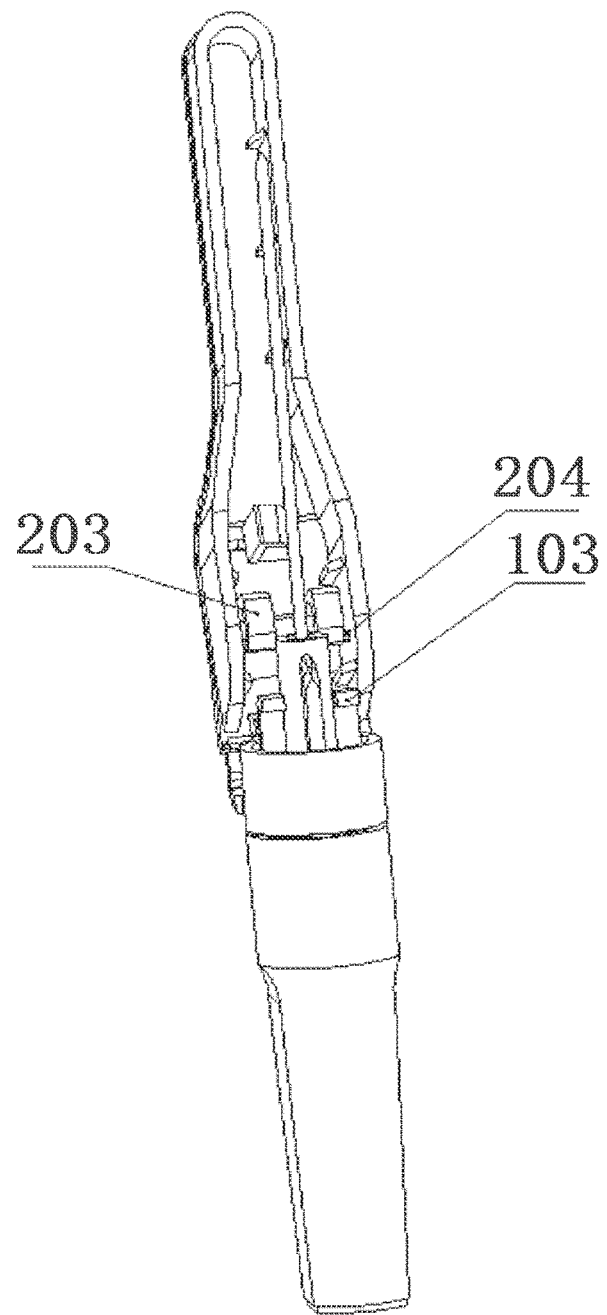
FIG. 8 is a perspective view of the first embodiment according to the present invention.
Figure 9:
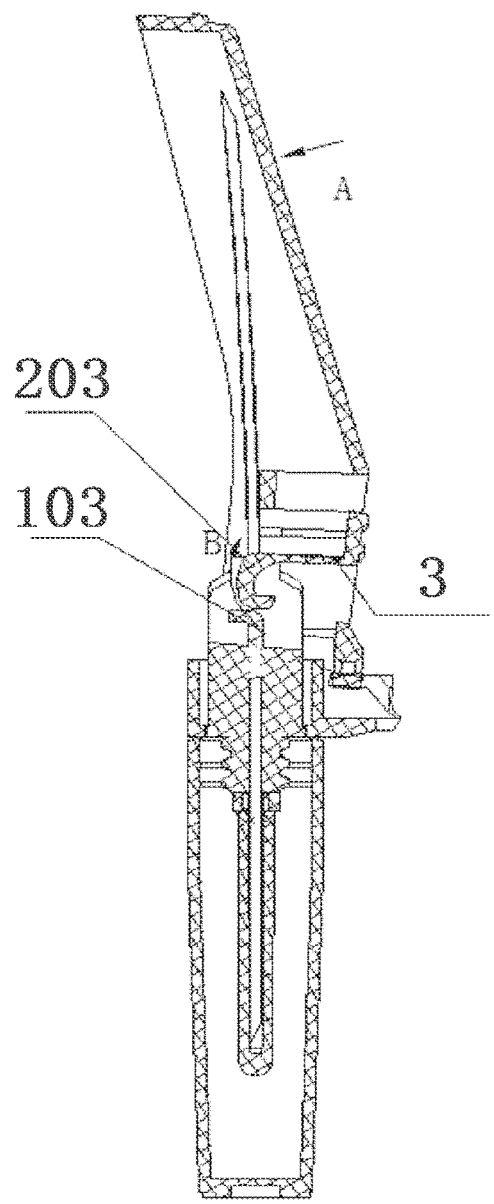
FIG. 9 is a diagram showing a first use state of the first embodiment according to the present invention.
Figure 10:
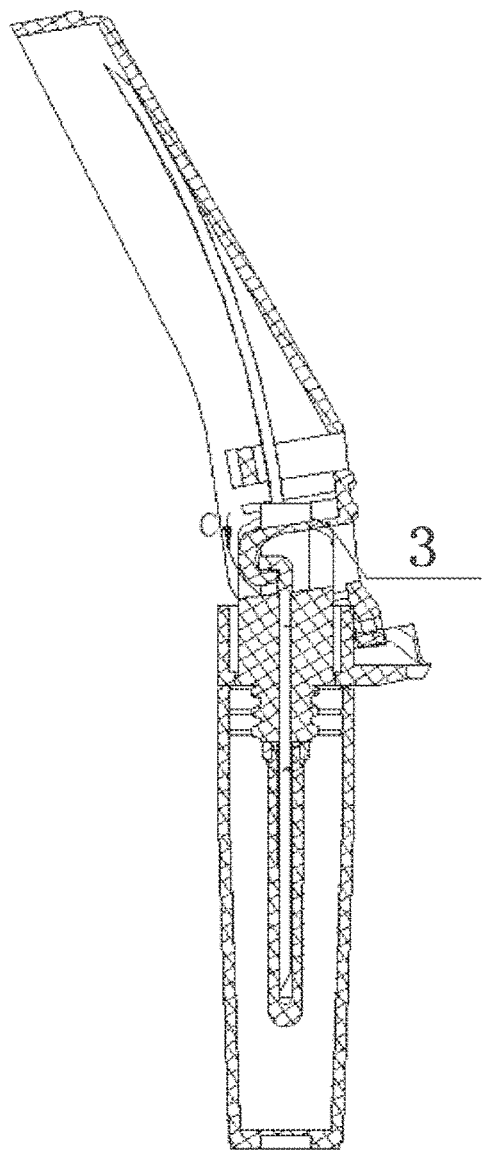
FIG. 10 is a diagram showing a second use state of the first embodiment according to the present invention.
Figure 11:
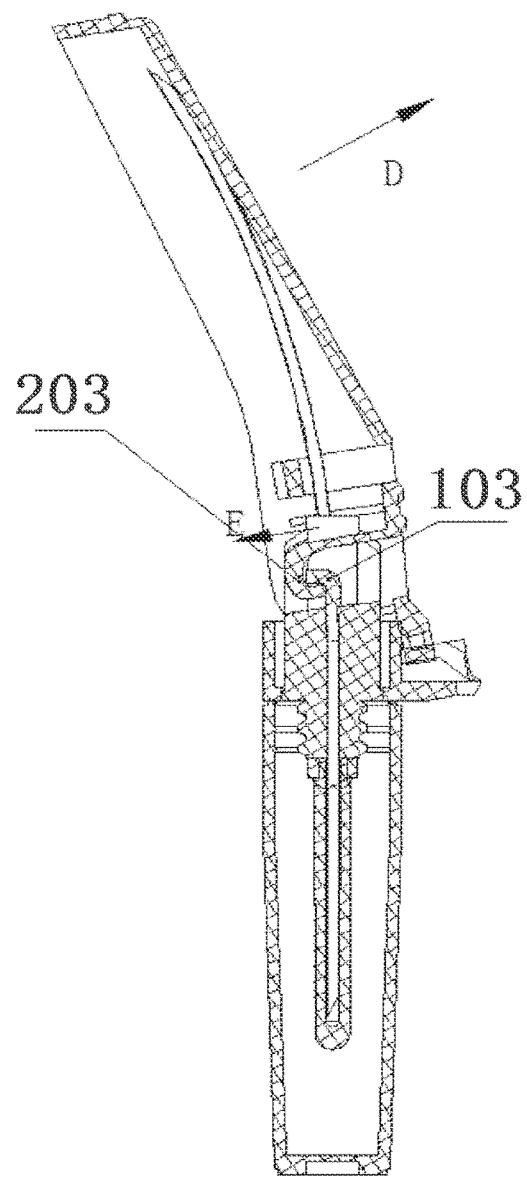
FIG. 11 is a diagram showing a third use state of the first embodiment according to the present invention.
Figure 12:
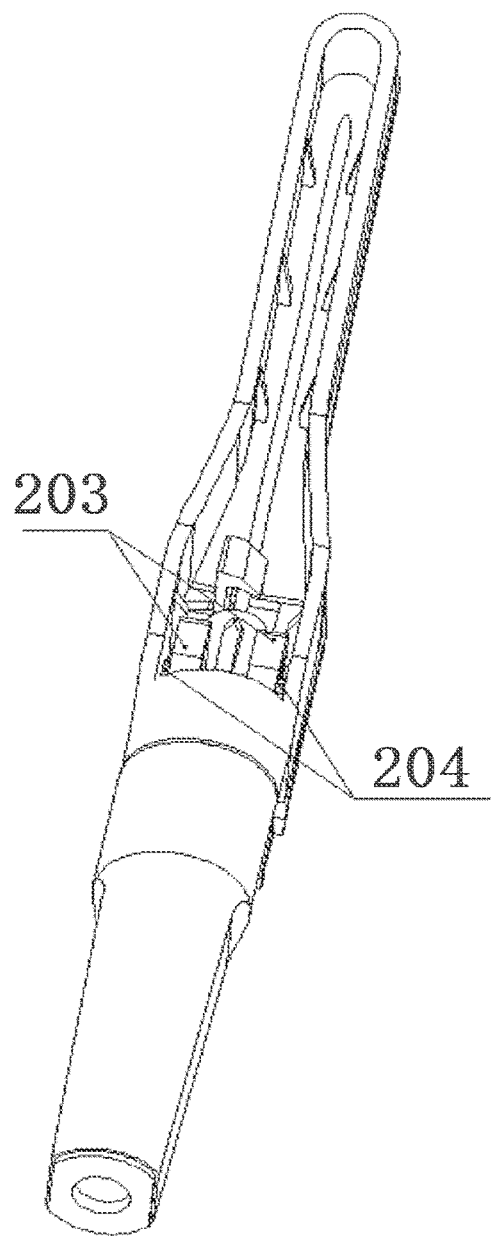
FIG. 12 is a schematic view showing a locked state of the injection needle and a safety protective cover according to the present invention.
Figure 13:
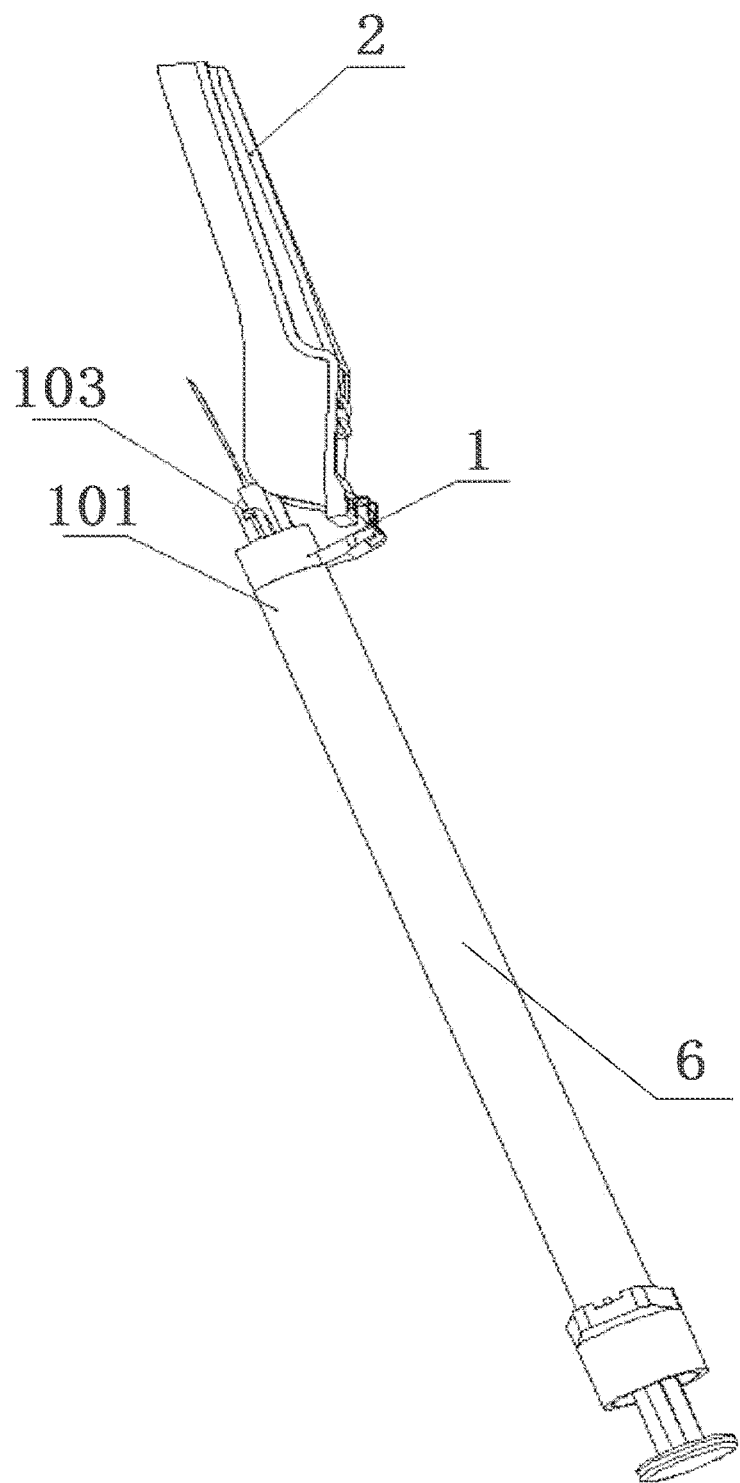
FIG. 13 is a schematic structural view of a second embodiment according to the present invention.
Figure 14:
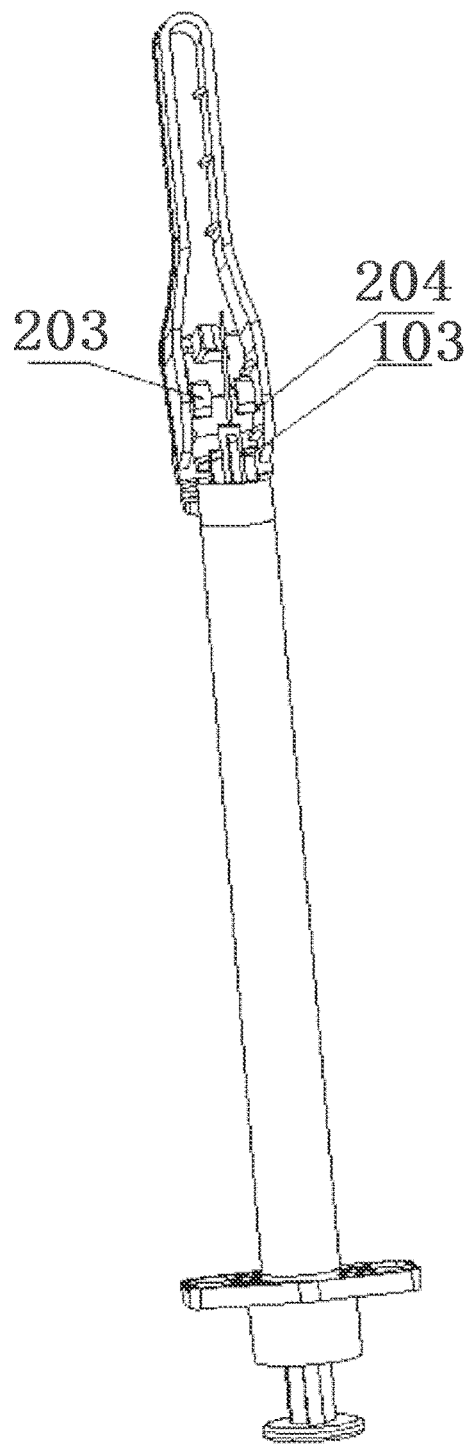
FIG. 14 is a perspective view of the second embodiment according to the present invention.
Figure 15:
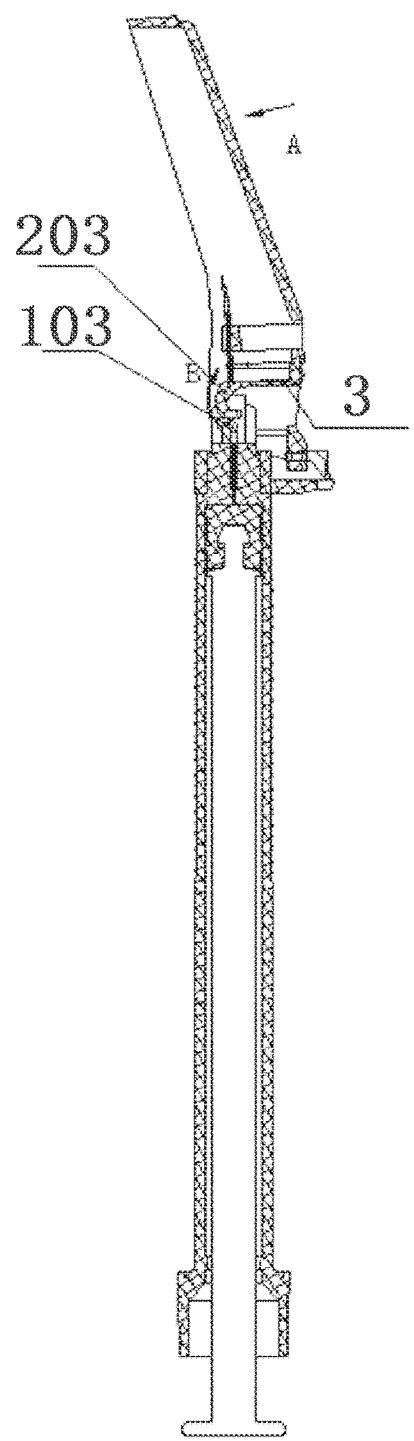
FIG. 15 is a diagram showing a first use state of the second embodiment according to the present invention.
Figure 16:
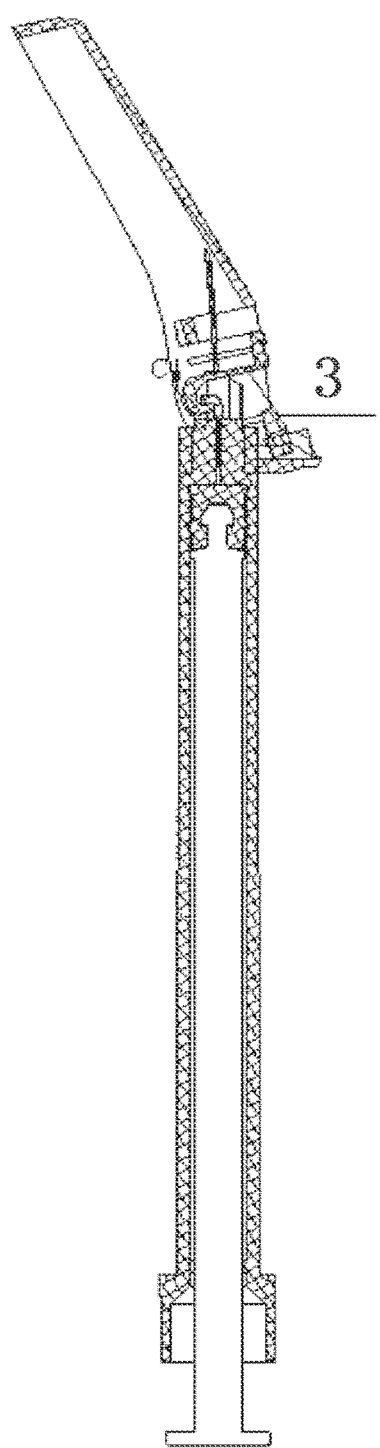
FIG. 16 is a diagram showing a second use state of the second embodiment according to the present invention.
Figure 17:
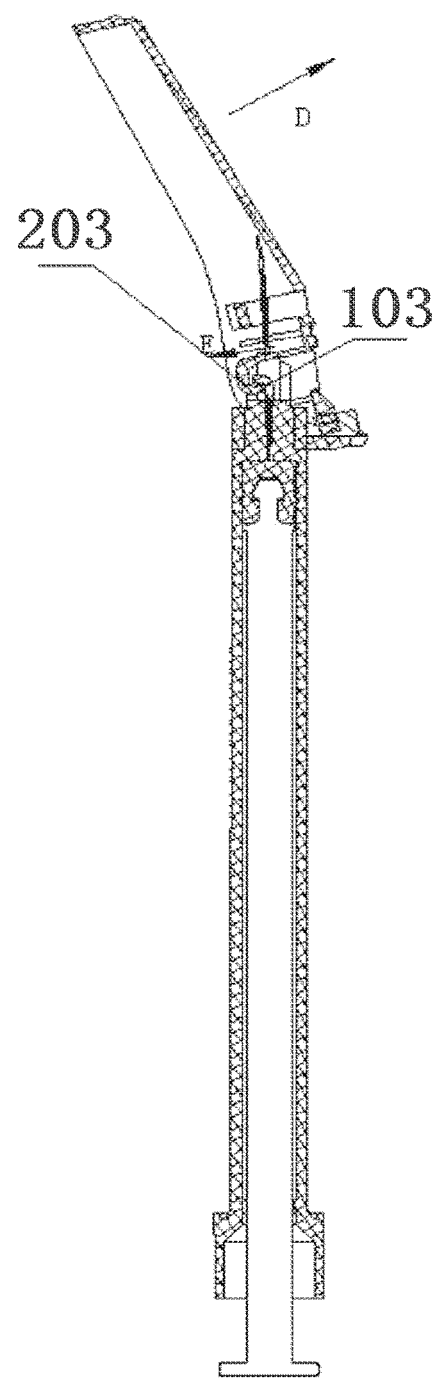
FIG. 17 is a diagram showing a third use state of the second embodiment according to the present invention.
Figure 18:
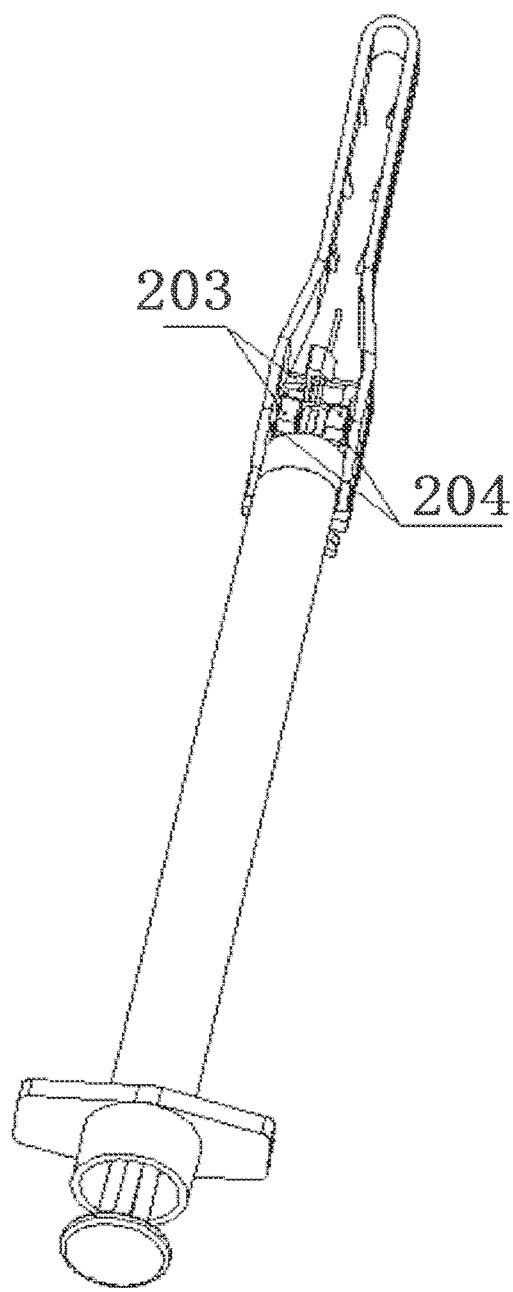
FIG. 18 is a schematic view showing a locked state of the injection needle and a safety protective cover according to the present invention.

In a specific operation process, as shown in FIG. 5 and FIG. 6, when the safety protective cover is pulled in the direction of a force D, the protective cover snap is caused to stretch in the direction of a force E so that the two protective cover snaps move toward both lateral sides, thereby causing the risk of disengagement. Therefore, in the present technical solution, the protective cover snap stoppers are additionally provided to block the protective cover snaps. Hence, the protective cover snaps only receive the force E, and the engagement state of the protective cover snaps and the needle hub hooks is not affected. Therefore, during practical use, the issue of disengagement is completely avoided, and the purpose of strengthening safety is achieved. The safety performance of the product is considered in terms of the magnitude of a force for disengaging the snaps from the hooks. The engagement between the protective cover snaps and needle hub hooks is a bard-type engagement and exhibits optimal stability and high firmness. A sole possibility of disengagement lies in the deformation or break of the snaps and hooks. It is known after tests and calculation and after consideration of properties of the material itself that the force for deformation and disengagement need to top 15N (with the force for disengaging the needle tube not being considered). It can be seen from this that both the safety coefficient and stability coefficient of the product itself reach an expected effect value.

In a first embodiment of the present invention, as shown in FIG. 7-FIG. 12, the injection needle 1 is connected to a blood collecting tube 5.

In a second embodiment of the present invention, as shown in FIG. 13-FIG. 18, the injection needle 1 is connected to an insulin pen 6.

Upon specific implementation, the needle hub hook 103 is formed through thermal deformation at an upper end of the reinforcing rib 104. It is characterized in that the mold is simple in structure, an out-of-mold rate is high and the thermal deformation is completed upon the assembling of the products.

Upon specific implementation, the needle hub hook 103 is formed by using a half mold at the upper end of the reinforcing rib 104. It is characterized in that it may be injection molded one time.

The above content is further detailed description of the present invention in conjunction with specific preferred embodiments, and cannot be believed that specific implementations of the present invention are only limited to the above depictions. Those having ordinary skill in the art, without departing from the inventive concept, may also make several simple derivations or substitutions, which should all be considered as falling within the protection scope of the present invention.

What is claimed is:

1. A safety injection needle, comprising: an injection needle comprising a needle hub and a needle tube, wherein the needle hub is connected to a safety protective cover via an elastic flip mechanism, two symmetrically-distributed needle hub hooks are disposed on a sidewall of the needle hub, the safety protective cover is an elongated structure as a whole, an inner cavity of the safety protective cover is hollow, a lower end of the safety protective cover is connected to one end of the elastic flip mechanism, an other end of the elastic flip mechanism is fixedly connected to the sidewall of the needle hub, an upper end of the safety protective cover is in a suspended shape, the safety protective cover is configured to flip as the elastic flip mechanism flips, a first side of the safety protective cover adjacent to the needle tube forms an opening, a second side of the safety protective cover opposite to the opening forms a closed surface, two symmetrically-distributed protective cover snaps are disposed in the hollow inner cavity of the safety protective cover, each of the two symmetrically-distributed protective cover snaps cooperate with each of the two symmetrically-distributed needle hub hooks, and a protective cover snap stopper is disposed on an outside surface of each of the two symmetrically-distributed protective cover snaps;

wherein an upper end portion of each of the two symmetrically-distributed needle hub hooks forms a hook end bent towards a side, each of the two symmetrically-distributed protective cover snaps comprises an elastic root portion and a snap end, the snap end of each of the two symmetrically-distributed protective cover snaps forms a bend towards the closed surface, initial contact points of each of the two symmetrically-distributed needle hub hooks and each of the two symmetrically-distributed protective cover snaps are a bend of the hook end and a bend of the snap end, and the hook end and the snap end bend in opposite directions, wherein when the hook end engages with the snap end, the closed surface comes into contact with the needle tube, ensuring that the needle tube curves under a pressure.

2. The safety injection needle according to claim 1, wherein when the hook end engages with the snap end, the protective cover snap stopper limits the snap end of the protective cover snap between an edge of the safety protective cover and the needle hub so that the snap end of the protective cover snap cannot deviate to left and right, preventing the protective cover snap from sliding away from both sides of the two symmetrically-distributed needle hub hooks, and the protective cover snap cooperates with the protective cover snap stopper on both sides to form a continuous blocking structure.

3. The safety injection needle according to claim 1, wherein the elastic flip mechanism comprises a fixed connection plate and a right-angle connection plate, a first end of the fixed connection plate is fixedly connected to the sidewall of the needle hub, a second end of the fixed connection plate is connected to a first end of the right-angle connection plate, a second end of the right-angle connection plate is fixedly connected to the lower end of the safety protective cover, a fold line is formed at a position where the fixed connection plate is connected to the right-angle connection plate, and the right-angle connection plate is configured to flip along the fold line.

4. The safety injection needle according to claim 1, wherein a reinforcing rib is disposed on an outer wall of the needle hub on each of two sides of an upper segment of the needle hub, and each of the two symmetrically-distributed needle hub hooks is disposed at a top end of the reinforcing rib.

5. The safety injection needle according to claim 1, wherein the closed surface comprises an upper portion and a lower portion, a continuous arc-shaped surface is disposed at a position where the upper portion is connected to the lower portion, and an inner angle smaller than 178 degrees and larger than 120 degrees is formed between the upper portion and the lower portion.

6. The safety injection needle according to claim 1, wherein a needle tube fixing hook is disposed in the hollow inner cavity of the safety protective cover, and the needle tube fixing hook cooperates with the needle tube.

7. The safety injection needle according to claim 1, wherein the injection needle is connected to a blood collecting tube.

8. The safety injection needle according to claim 1, wherein the injection needle is connected to an insulin pen.

9. The safety injection needle according to claim 1, wherein a reinforcing rib is respectively disposed on an outer wall on each of both sides of an upper segment of the needle hub, and each of the two symmetrically-distributed needle hub hooks is formed through thermal deformation at an upper end of the reinforcing rib.

10. The safety injection needle according to claim 1, wherein a reinforcing rib is respectively disposed on an outer wall on each of both sides of an upper segment of the needle hub, and each of the two symmetrically-distributed needle hub hooks is formed by using a half mold at an upper end of the reinforcing rib.

* * * * *